United States Patent
Neary (10) Patent No.: US 9,778,169 B2
(45) Date of Patent: Oct. 3, 2017

(54) TWIST DELAMINATION TEST

(71) Applicant: VERMEER MANUFACTURING COMPANY, Pella, IA (US)

(72) Inventor: Andrew Jeffrey Neary, Knoxville, IA (US)

(73) Assignee: VERMEER MANUFACTURING COMPANY, Pella, IA (US)

( * ) Notice: Subject to any disclaimer, the term of this patent is extended or adjusted under 35 U.S.C. 154(b) by 0 days.

(21) Appl. No.: 15/303,808

(22) PCT Filed: Apr. 17, 2015

(86) PCT No.: PCT/US2015/026439
§ 371 (c)(1),
(2) Date: Oct. 13, 2016

(87) PCT Pub. No.: WO2015/161232
PCT Pub. Date: Oct. 22, 2015

(65) Prior Publication Data
US 2017/0030826 A1  Feb. 2, 2017

Related U.S. Application Data

(60) Provisional application No. 61/981,361, filed on Apr. 18, 2014.

(51) Int. Cl.
*G01N 3/24* (2006.01)
*G01N 19/04* (2006.01)
*G01N 3/22* (2006.01)

(52) U.S. Cl.
CPC ............... *G01N 19/04* (2013.01); *G01N 3/22* (2013.01)

(58) Field of Classification Search
CPC ........ G01N 15/08; G01N 11/00; G01N 19/06; G01N 3/24; G01B 5/28; G01D 1/16
USPC .............................. 73/38, 788, 105, 783, 790
See application file for complete search history.

(56) References Cited

U.S. PATENT DOCUMENTS

| 6,532,805 B1 | 3/2003 | Kokawa et al. |
| 9,016,136 B1 * | 4/2015 | Stamatoukos ......... G01N 19/04 73/150 A |
| 2009/0136760 A1 | 5/2009 | Bourgeois |
| 2011/0174056 A1 | 7/2011 | Liggett et al. |
| 2013/0042670 A1 * | 2/2013 | Greenberg ............. G01N 15/08 73/38 |

(Continued)

FOREIGN PATENT DOCUMENTS

| JP | 11-258131 A | 9/1999 |
| JP | 2006-047074 A | 2/2006 |
| WO | WO 2015/161232 | 10/2015 |

OTHER PUBLICATIONS

International Search Report and Written Opinion for International Application No. PCT/US2015/026439, Search completed Jul. 30, 2015, Mailed Jul. 30 2015, 13 Pgs.

*Primary Examiner* — Jewel V Thompson
(74) *Attorney, Agent, or Firm* — Lathrop Gage LLP (57) ABSTRACT

Devices and methods for testing for delamination of a coating applied to a substrate and related test pieces are provided. The methods can in fixing one end of a coated test piece and then twisting the other end of the test piece about its longitudinal axis a predetermined amount. The test methods can provide a simple and rapid means of quality control with respect to coating (e.g., paint) adherence, especially on metal edges.

20 Claims, 6 Drawing Sheets

(56) References Cited

U.S. PATENT DOCUMENTS

2014/0013825 A1* 1/2014 Liu .................... G01N 15/0826
73/38

* cited by examiner

TWIST DELAMINATION TEST

CROSS-REFERENCE TO RELATED APPLICATIONS

This application is a 35 U.S.C. §371 filing of International Application No. PCT/US2015/026439, filed Apr. 17, 2015, which claims the benefit of U.S. Provisional Application No. 61/981,361, filed Apr. 18, 2014, each of which is hereby incorporated by reference in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND

Painted or coated metal parts are known to have the potential to experience a certain amount of delamination during use, especially along part edges. Such delamination (e.g., peeling, chipping, etc.) may occur unreasonably prematurely in the lifecycle of a given painted part due to presence of oxides on the base metal (e.g., due to laser cutting of a given metal part), surface roughness, insufficient cleaning of a part prior to painting, etc. Too much delamination occurring in too short of a time frame (e.g., within a warranty time frame) when placed into use by a customer may lead to a warranty claim, and the necessary repainting or replacement, in turn, would correspond to lost profits.

Various mechanical tests have been developed that help test the adhesive limits of paint on metallic parts. For example, ISO adhesive strength tests which involve mechanical stress application on the coating include pull-off tests, twist-off tests and peel-off tests. ISO tests which involve deformation of test specimens include bend tests with variously shaped mandrels, three point bend tests, t-bend tests, and cupping tests.

BRIEF SUMMARY

In an aspect, the invention provides methods for testing for delamination of a coating applied to a substrate. The methods of the invention can quickly stress a coated metal test piece to a level that would likely exceed the stress that a production part would see over its warranty period. Therefore, the methods described herein can provide a simple and rapid means of quality control with respect to coating (e.g., paint) adherence, especially on metal edges. In other aspects, the invention provides useful test pieces and devices for use in the methods of the invention.

In an embodiment, the test piece comprises a substrate piece fabricated of a sheet of metal at least partially coated with a coating. In an embodiment, at least some of the attributes of the test piece are selected to correspond to those of a chosen production part. In an embodiment, the metallic sheet substrate piece may be formed of the same metal composition and coated with the same coating composition as the chosen production part. In embodiments, the coating is a polymer coating, a paint coating, or an electroplated coating. In a further embodiment, the test piece is formed to shape in the same matter as the chosen production part. For example, the metallic sheet substrate piece may be cut from the sheet metal using a laser or with a blanking die. In an additional embodiment, the metallic sheet substrate piece is surface treated prior to coating in a similar manner to the production part. For example, at least some of the edges of the metallic sheet substrate piece may be subjected to an oxide removal step prior to surface coating; such treatment may be used to remove oxides resulting from the laser cutting process.

Figure 1A:
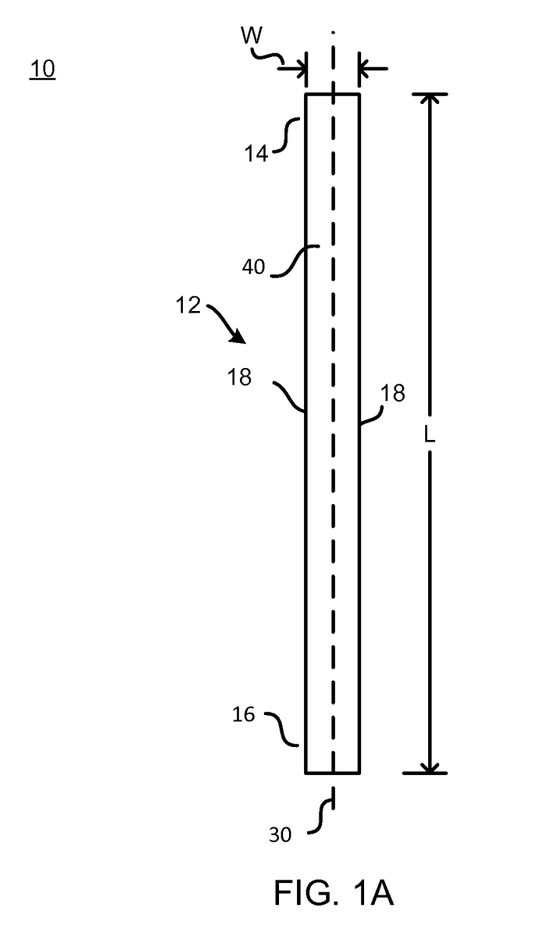
FIG. 1A shows a schematic top view of an uncoated metallic sheet substrate according to one embodiment of the current invention.
Figure 1B:
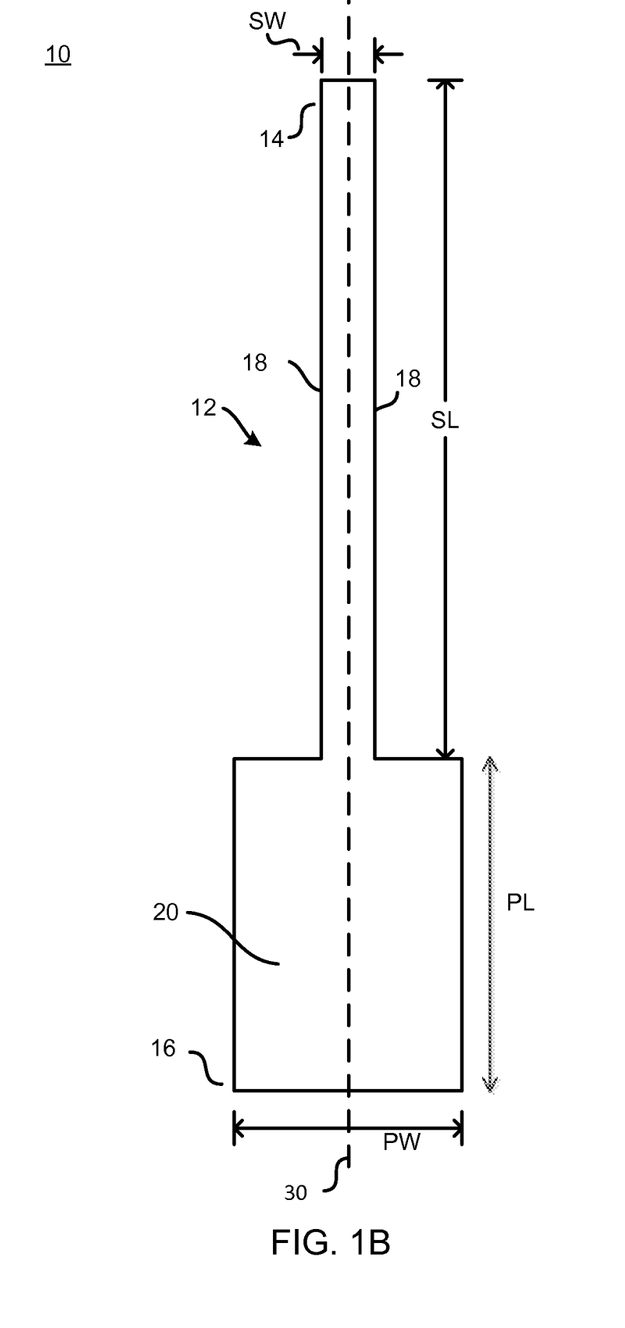
FIG. 1B shows a schematic top view of another uncoated metallic sheet substrate.

In an embodiment, the metallic sheet substrate piece is elongated and characterized by a substrate piece length, a longitudinal axis, a pair of opposed faces defining the substrate piece thickness, a pair of opposed longitudinal edges, and a first and a second end. These features are schematically illustrated in FIGS. 1A and 1B, which show two different substrate piece configurations. In embodiments, the thickness of the substrate piece is from 0.75 mm to 6.5 mm, from 1.0 mm to 6.5 mm, from 1.25 mm to 6.5 mm, from 1.5 mm to 6.5 mm, from 1.0 mm to 3.0 mm, from 1.0 mm to 2.0 mm, from 1.25 mm to 3.0 mm or from 1.25 to 2.0 mm.

FIG. 1A shows a configuration in which the substrate piece 10 is the form of a generally rectangular strip. The substrate piece length is indicated by the label L and the substrate piece width by the label W. The longitudinal axis is indicated by label 30. Only one of the opposed faces 40 (the top face) is shown in FIG. 1A. The opposed longitudinal edges are labeled as 18. The first end of the substrate piece is indicated by label 14 and the second end by label 16. The thickness of the substrate piece, T, is not shown in this view.

FIG. 1B shows a substrate piece configuration comprising a generally rectangular substrate strip portion 12 joined to a substrate plate portion 20. The length of the substrate strip portion is indicated by the label SL and the width of the substrate strip portion by the label SW. The width of the substrate plate portion is indicated by the label PW and the length of the substrate plate portion by the label PL. In a further embodiment (not illustrated), the substrate piece comprises a first substrate plate portion attached to one end of the substrate strip portion and a second substrate plate portion attached to the other end of the substrate strip portion. In an embodiment, the substrate plates have the same dimensions and proportions as described herein for a single substrate plate.

In an embodiment, the invention provides a metallic sheet substrate piece which is elongated and characterized by a substrate length, a longitudinal axis, a pair of opposed faces defining the substrate thickness, a pair of opposed longitudinal edges, and a first and a second end. In an embodiment, the metallic sheet substrate piece comprises a substrate strip portion and a substrate plate portion connected to one end of the substrate strip portion. Each of the substrate strip portion and the substrate plate portion may be characterized by a width and a length. In an embodiment, the substrate strip width is less than the substrate plate width. In a further embodiment, the substrate strip length is greater than the substrate plate length. In an embodiment, the width of the substrate strip portion is at least twice the thickness of the substrate piece, the length of the substrate strip portion is at five times the width of the substrate strip portion; and the width of the substrate plate portion is at least twice the width of the width of the substrate strip portion. In a further embodiment, the width of the substrate plate portion is at least twice the width of the substrate strip portion. In an embodiment, the length of the strip section is 1.5 to 10 times, 1.5 to 5 times or 2.0 times the length of the plate section. In embodiments, the thickness of the metallic sheet substrate is from 20 gauge to 0.25 inches, 16 gauge to 0.25 inches or 14 gauge to 0.25 inches, the strip width is from 0.5 to 3 inches (approximately 12.7 mm to 76.2 mm), and the strip length is from 4 to 36 inches (approximately 10.1 cm to 91.4 cm) or from 6 to 18 inches (approximately 15.2 cm to 45.72 cm).

In an embodiment, application of the coating to the metallic sheet substrate piece produces a test piece similar in form to the metallic sheet substrate piece. In an embodiment, the coated test piece is elongated and characterized by a test piece length, a longitudinal axis, a pair of opposed faces defining the test piece thickness, a pair of opposed longitudinal edges, and a first and a second end. In an embodiment, the test piece comprises a strip portion characterized by a strip width and a strip length connected to a plate portion characterized by a plate width and plate width, the strip width being less than the plate width. In a further embodiment, the strip length is greater than the plate width.

In an embodiment, the invention provides a test piece,
the test piece being elongated and characterized by a test piece length, a longitudinal axis, a pair of opposed faces defining the test piece thickness, a pair of opposed longitudinal edges, and a first and a second end;
the test piece comprising a metallic sheet substrate at least partially coated with a coating and further comprising:
a strip portion characterized by a strip width and a strip length, the width of the strip portion being at least twice the test piece thickness and the length of the strip portion being at five times the width of the strip portion; and
a plate portion located at one of the first and the second end of the test piece and connected to the strip portion, the width of the plate portion being at least twice the width of the width of the strip portion.
wherein at least the opposed faces and the opposed longitudinal edges of the strip portion of the test piece are coated with the coating.

Figure 2:
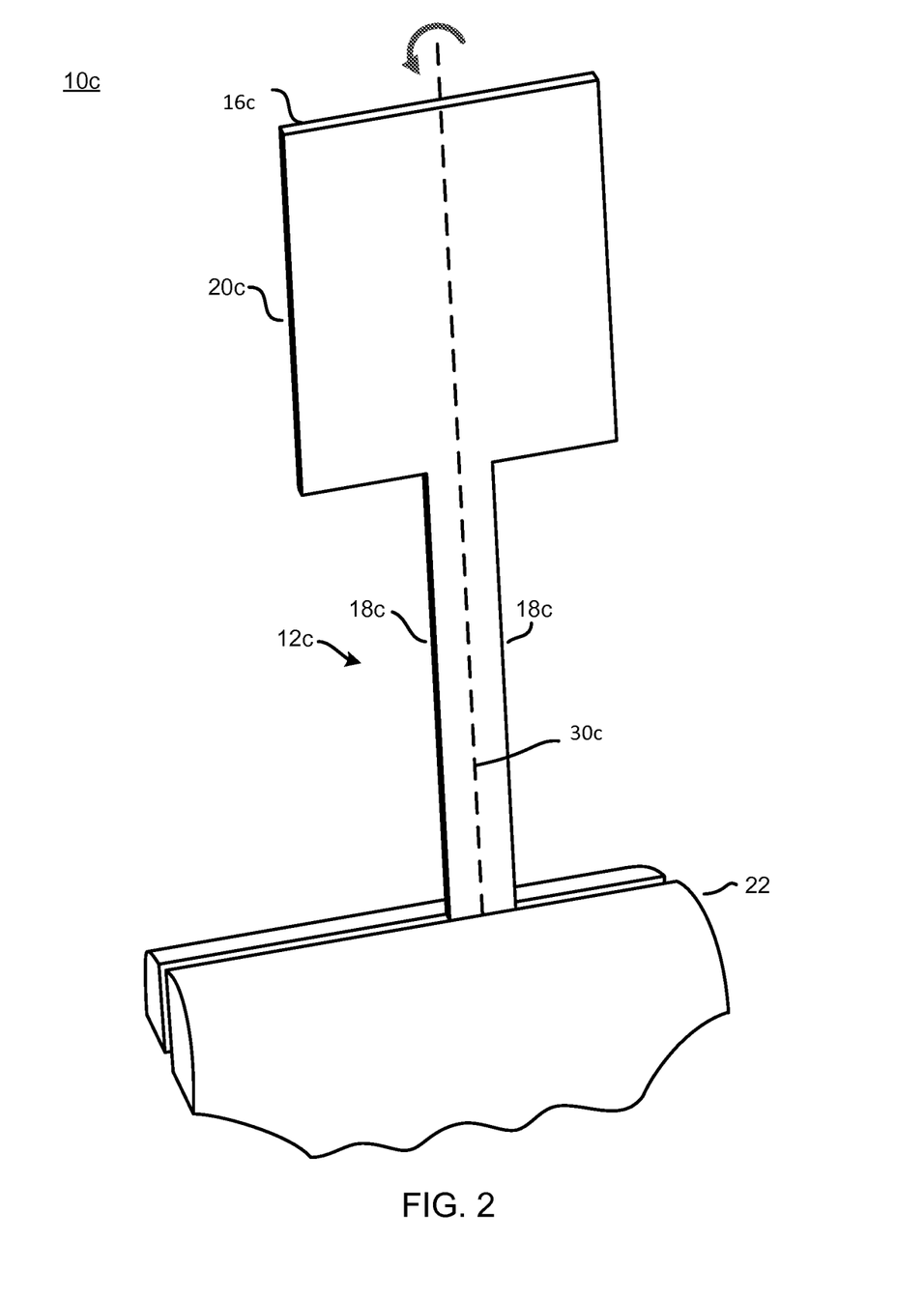
FIG. 2 shows a schematic front view of a coated test piece loaded in a vise, prior to twisting, according to one embodiment of the current invention. An exemplary direction of rotation is also shown.

In an embodiment of the testing process, one of the ends of the coated test piece 10c is fixed. For example, the first end of the test piece is mounted in a fixture 22 such that a remainder portion of the test piece extends away from the fixture, as illustrated in FIG. 2. The coated test piece 10c in FIG. 2 is similar in form to the test piece 10 shown in FIG. 1B. In an embodiment, mounting the first end of the test piece in a fixture (such as a vise or a clamp arrangement) establishes a first constrained portion at the first end of the test piece, the first constrained portion being associated with a first constrained length.

In an embodiment, the second end 16c of the test piece is gripped, but is not fixed in place, during the testing process. Gripping the second end of the test piece establishes a second constrained portion at the second end of the test piece, the second constrained portion being associated with a second constrained length. The free length of the test piece is defined herein as the length of the test piece between the first and second constrained lengths of the test piece.

In an embodiment, while the first end of the test piece is fixed and the second end of the test piece is gripped, the second end of the test piece is twisted a defined rotational amount about the longitudinal axis 30c. The curved arrow in FIG. 2 schematically illustrates counter-clockwise rotation; in further embodiments the test piece is rotated in a clockwise direction. In an embodiment, the rotation is from 180 to 1080 degrees. In an embodiment, the amount of rotation is less than the amount which would cause the test piece to buckle back on itself such that one of the longitudinal edges hits the another; such buckling can be undesirable (e.g. can cause additional delamination). In embodiments, the amount of rotation is less than two full revolutions (less than 720 degrees), from 360 degrees to less than 720 degrees, from 450 degrees to less than 720 degrees or from 540 degrees to less than 720 degrees. In embodiment, the amount of rotation is from 360 degrees to 650 degrees, from 450 degrees to 650 degrees or from 540 degrees to 650 degrees. In further embodiments, the amount of revolution is measured to the nearest quarter revolution and is from 360 degrees to 630 degrees, from 450 degrees to 630 degrees or from 540 degrees to 630 degrees.

Figure 3A:
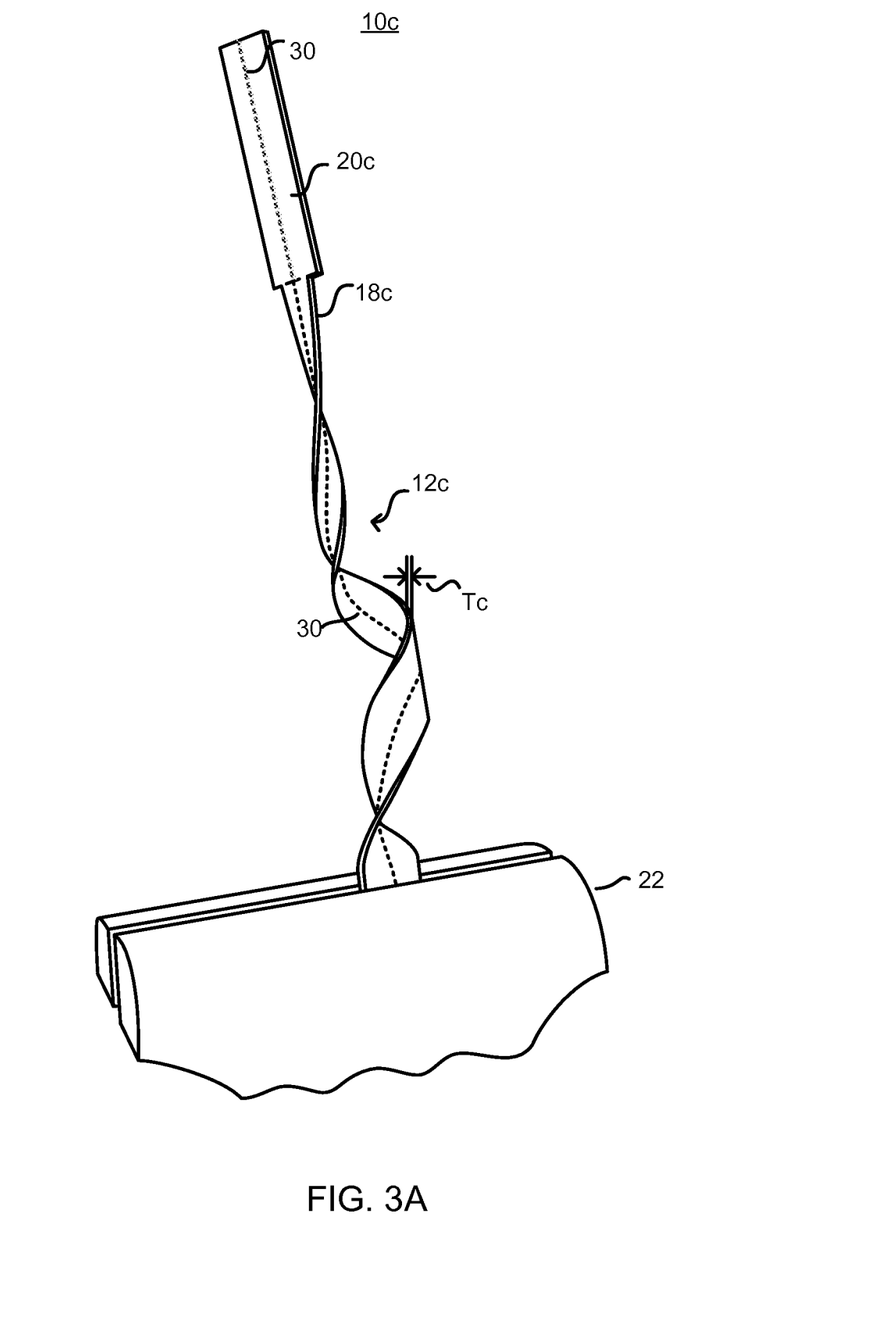
FIG. 3A shows a schematic front view of the vise-loaded coated test piece of FIG. 2, after twisting approximately 1.75 rotations.
Figure 3B:
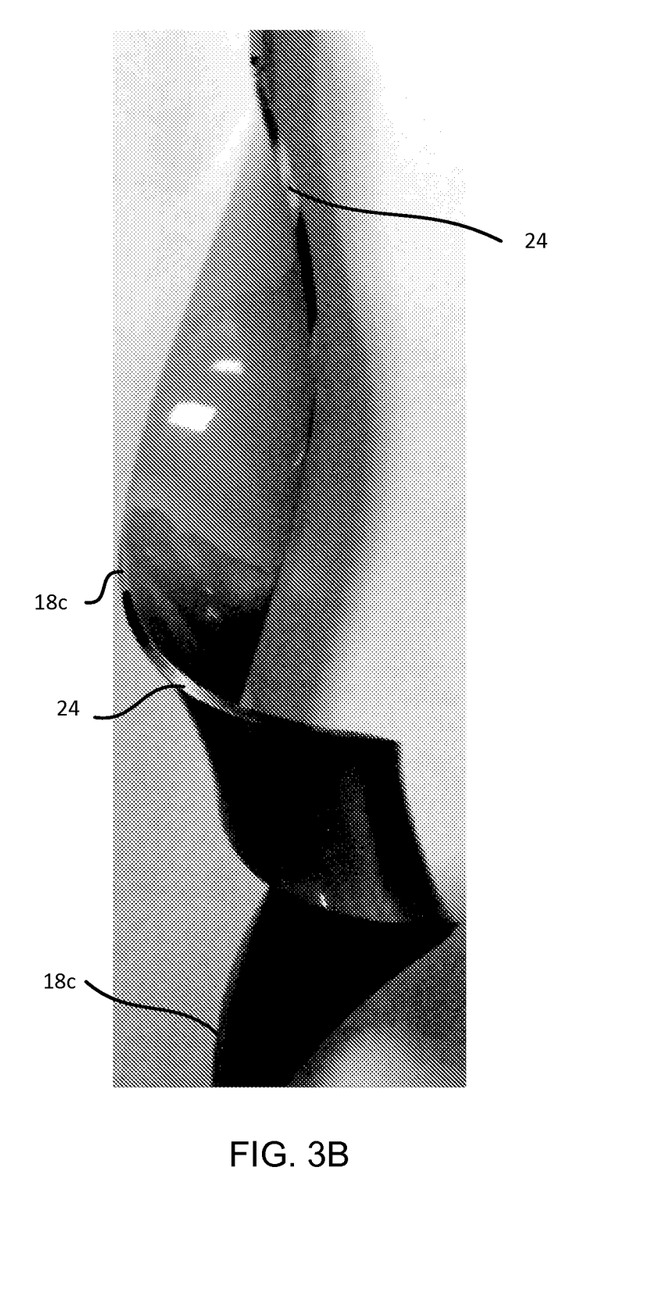
FIG. 3B illustrates a portion of a coated test piece after testing. Delaminated edge portions (24) are visible.

As illustrated in FIGS. 3A and 3B, rotation of the plate portion of the test piece can result in twisting and deformation of the strip portion of the test piece. Therefore, the rotation of the coated test piece is defined about the longitudinal axis of the test piece at the second (plate) end of the test piece. Each coated edge 18c in the portion of the test piece being measured is then observed for any delaminated edge portions after the twisting step. FIG. 3B illustrates a photograph of a test piece after testing; both coated edge portions (18c) and delaminated edge portions (24) are indicated. FIG. 3A illustrates the coated test piece thickness as Tc. In additional embodiments, the delaminated area along the edges and/or the faces is measured.

In an embodiment, the sum of the delaminated edge lengths or face areas is compared to a total edge length or a total face area of the test over a given measurement region of the test piece. In an embodiment, the total edge length and/or face area over a given measurement region is measured before testing, since this can be more convenient than performing these measurements on the deformed part. In an embodiment suitable for measurement of delamination on a test piece which has the form of a generally rectangular strip, the length of the measurement region is selected as the free length of the test piece. In an embodiment suitable for a test piece comprising a plate portion connected to a strip portion, the length of the measurement portion is selected as the length of the free region of the strip portion of the sample (e.g. defined between the end of the mounting fixture and the junction of the strip portion and the plate portion). In an embodiment, the relative widths of the plate portion and the strip portion and the extent of rotation are selected so that significant deformation of the coated test piece occurs in the strip portion of the coated test piece.

In an embodiment, the invention provides a method for testing for delamination of a coating from a test piece, the method comprising the steps of:
a. Providing a test piece comprising a metallic sheet substrate at least partially coated with a coating, the test piece being elongated and characterized by a test piece length, a longitudinal axis, a pair of opposed faces defining the test piece thickness, a pair of opposed longitudinal edges, and a first and a second end;
b. Establishing a first constrained portion at the first end of the test piece by mounting the first end of the test piece in a fixture, the first constrained portion having a first constrained length;
c. Establishing a second constrained portion at the second end of the test piece by gripping the second end of the test piece, the second constrained portion having a second constrained length, thereby also establishing a free length of the test piece between the first and second constrained lengths;
d. While maintaining the first and second constrained lengths of steps b and c, twisting the second end of the test piece by rotating the second end of the test piece a predetermined amount about the longitudinal axis at the second end of the test piece, thereby also twisting at least a portion of the free length of the test piece;

e. After step d, measuring at least one of:
the total delamination length on the pair of opposed longitudinal edges over a measurement portion of the free length of the test piece; and
the total delamination area on the pair of opposed faces over a measurement portion of the free length of the test piece;

f. Comparing at least one of:
the total delamination length of step e to the total length of the pair of opposed longitudinal edges over the measurement portion of free length of the test piece; and
the total delamination area of step e to the total area of the opposed faces over the measurement portion of the free length of the test piece.

In an embodiment, the ratio of the total delamination length over the measurement portion of the coated test piece to the total length of the pair of opposed longitudinal edges over the measurement portion of the coated test piece is compared to a baseline value. In embodiments, the test piece passes the test when the amount of delamination is less than or equal to the baseline value. In embodiments, the baseline value is 30% or 20%.

DETAILED DESCRIPTION OF THE INVENTION

Associated with the methods of testing described above, it is to be understood that there may be a series of precursor steps. First, the substrate piece may be manufactured from a sheet of metal using a specific manufacturing method (e.g., a laser cutting operation). The substrate piece may then be prepared with a specific preparation process (e.g., chemical and/or mechanical cleaning/surfacing finishing). Once ready, the substrate piece may be coated employing a specific coating process (e.g., spray painting; electrochemical plating; etc.). The manufacturing, preparation, and coating steps may all be chosen to simulate a series of larger scale production steps (e.g., as part of a quality assurance check).

In embodiments, the substrate piece for the test piece is fabricated from a metallic sheet. In an embodiment, a metallic sheet primarily comprises a metal or metal alloy, but may further comprise minor amounts of surface oxides and other non-metallic components. The metallic sheet may be sheet metal. In embodiments, the sheet metal may be selected from the group consisting of steel, aluminum and aluminum alloys. It is, however, to be understood that the sheet metal may be selected from any metal or alloy that may be employed in a given sheet metal fabrication. In an embodiment, the test piece is cut from the sheet metal using a laser cutting process. Other cutting techniques known to the art, including blanking with a blanking die, may also be used.

FIGS. 1A-1B illustrate two different substrate 10 configurations. In embodiments, the metallic sheet substrate 10 is made of a similar metal (e.g., steel, aluminum, aluminum alloy, etc.) and of a comparable gauge thickness (e.g., 14-16 ga to 0.25 in) as a sheet metal being used and painted and/or otherwise coated in production. In further embodiments, the metallic sheet substrate 10 is formed/sized in the same manner as the sheet metal being employed, which can, for example, mean being laser cut to shape.

Sheet metal subjected to laser cutting typically is prone to oxidation and/or surface anomalies/roughness where new edges are formed, and newly formed edges may also become contaminated with dirt, dust, etc. Surface oxidation, anomalies, contamination, etc., may all contribute to reduce the ability of paint and/or another coating to adhere thereto (i.e., seen as paint/coating delamination over the long term). To maximize adherence and minimize delamination, it is common to subject the cut metal part to a surface treatment such as a chemical bath, sandblasting, and/or another chemical and/or mechanical polishing step (especially along the newly formed edges). Accordingly the as-formed metallic sheet substrate 10 is subjected to similar post-processing as would be seen in regular production, prior to coating and/or painting thereof, in order to mimic production conditions as best as possible. By way of example only, the laser cut metallic sheet substrate 10 may be chemically washed and rinsed and then top-coated (e.g., painted), with the top coat then cured for a sufficient time (e.g., one week). After a sufficient cure time were to elapse, the metallic sheet substrate 10 would be ready for testing.

As shown in FIGS. 1A and 1B, the metallic sheet substrate is elongate and is characterized by a substrate length L; a longitudinal axis 30; a pair of opposed faces 40; together defining the substrate thickness T; and a pair of opposed longitudinal edges 18. The first end 14 and the second end 16 of the metallic sheet substrate are also shown. As shown in FIGS. 1A and 1B, the metallic sheet substrate 10 includes an elongate substrate strip section 12, with the elongate substrate strip section 12 defining a first substrate strip end and a second strip end. In the configuration of FIG. 1A, the first and second substrate strip ends are the same as the first and second ends of the test piece. The elongate substrate strip section 12 has a substrate strip length SL, and a substrate strip width SW. Typically the substrate strip thickness ST is the same as the substrate thickness. The pair of elongate edge portions 18 in the strip region of the substrate are associated with the strip thickness ST. In one example, the elongate substrate strip section 12 may have a substrate strip thickness ST of 16 ga to 0.25 in, a substrate strip length SL of 12 in, and a s substrate trip width SW of 1 in. More generally, the substrate strip length SL may be, e.g., at least five times greater than the strip width SW, to facilitate easy twisting of the elongate substrate strip section 12 and/or to provide a sufficient amount of substrate strip length SL for edge testing. To help standardize the test, all metallic sheet substrate 10 being used for process testing may further incorporate, at least, a constant substrate strip length SL and a constant substrate strip width SW to ease comparison between sample tests. (The gauge thickness may, of course, vary based on the type of sheet metal employed.) The metallic sheet substrate 10 may further provide an additional substrate grip plate section 20 as an extension of the second substrate strip end (e.g., an integral extension). The substrate grip plate section 20 may have a substrate plate width PW that is at least two times that of the substrate strip width SW (e.g., 2-4 in), in order to facilitate gripping thereof and twisting, e.g., with pliers (not shown), of the elongate substrate strip section 12. The additional width of the substrate plate width PW allows for a greater moment arm for twisting than is possible with the substrate strip width SW, as well as just generally providing a larger platform for gripping the metallic sheet substrate 10.

A coated or painted test piece, such as seen in FIGS. 2, 3A, 3B and 4, is generally designated as "10c" to distinguish from a metallic sheet substrate 10 which is not coated. In preparation for the twist delamination test of the present invention, the coated metal blank 10c is loaded into a fixture 22, such as a vise or other comparable clamping device. In the example illustrated, the first strip end 14c of the elongate strip section 12c of the coated metal blank 10c is held by the fixture 22. The amount of the first strip end 14c held by the fixture 22 may be, for example, the first 1-3 in of length of elongate strip section 12c or any suitable amount needed to hold the coated metal blank 10c sufficiently and stably in place during the twisting step. Of course, there is an advantage to minimizing the amount of the first strip end 14c being held so as to maximize the amount of the length (i.e., the remainder length or free length) of the elongate strip section 12c that is subjected to the twisting action of the current test (i.e., portion not directly held/gripped by the fixture 22). In an embodiment, the coated or painted test piece is characterized by the dimensions of the substrate test piece.

Once the first strip end 14c is affixed in the fixture 22, the coated metal blank 10c is ready to be subjected to the twisting action associated with the present test. While any suitable method may be used to twist the coated metal blank 10c, for purposes of illustration, the grip plate section 20c may be gripped (e.g., by pliers (not shown)) and subsequently be turned by a user performing the test, in order to thereby twist the coated metal blank 10c. Alternatively, the twisting process could, within the scope of the present test, be automated, which could aid in twist precision, number of parts to be tested in a given time frame, etc. In one embodiment, the coated metal blank 10c may be twisted through a defined number of rotations to induce a suitable level of stress at the coating/metal blank interface (not labelled). In particular, a suitable level of stress may, for example, one that mimics the stress level that may reasonably be expected to be endured during, e.g., the warranty period of a given painted component. Alternatively, the number of rotations could be chosen to apply a specific level of stress to a given edge 18c. That stress can be calculated knowing the elastic modulus (E) of the metal/alloy used for the metal substrate 10 and the amount of lengthwise strain created by the twisting (i.e., final SL−original SL), given the formula E=stress/strain. For illustrative purposes, 1.75 twist rotations was used, as the associated stress level generated was expected to meet or exceed the stress levels expected to be experienced at the coating/blank interface through the warranty period and/or to exceed the surface tension needed to cause paint/coating to delaminate from an oxidized metal surface (e.g., a lower threshold than for paint-to-metal, in most instances).

Once twisting is complete, it is then possible to view and measure the extent of the edge delamination induced by the twisting. To simplify viewing and measuring, one may run a finger, brush, etc., along the elongate edge portions 18c, in order to remove any coating/paint scale portions that popped or otherwise became dislodged by the twisting action but that did not totally separate from the coat/paint. Upon ascertaining the portions where the coating/paint separated from the coated metal blank 10c, each given delaminated edge portion 24 may then be measured. The delaminated edge portions 24, when occurring due to the presence of a laser-induced oxide layer on the base metal, tend to be shinier than the base metal of the metallic sheet substrate 10, which helps make these delaminated portions easy to identify.

Figure 4:
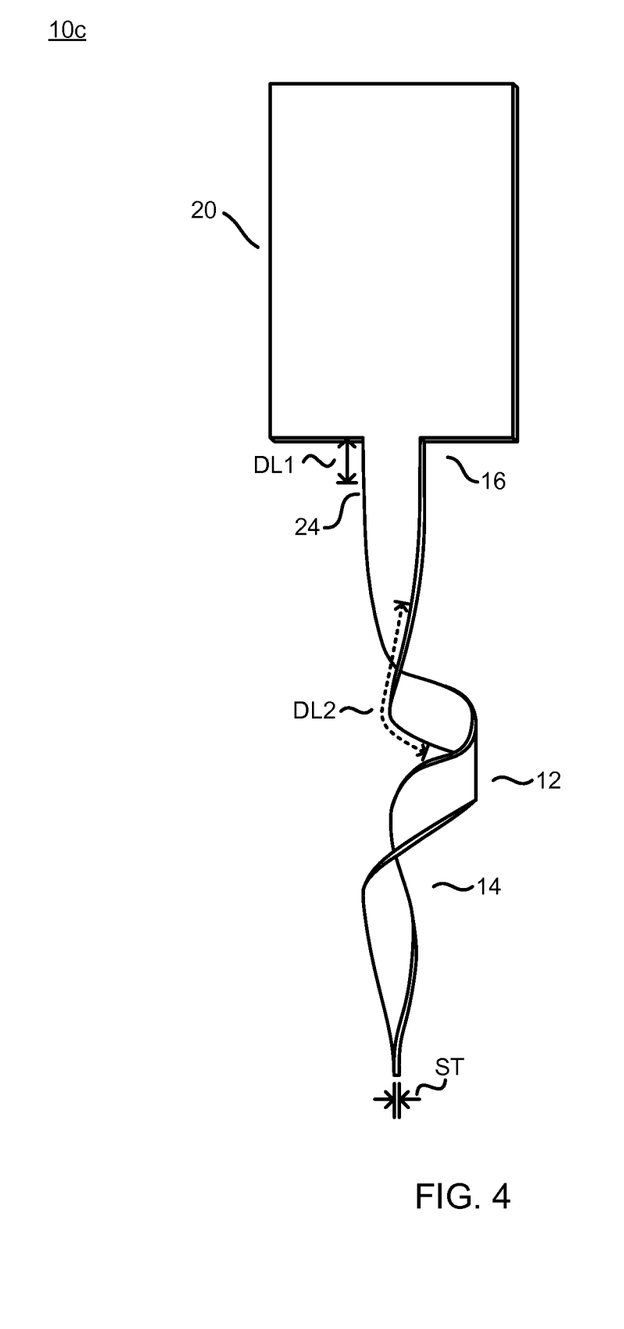
FIG. 4 provides a schematic illustration of a coated test piece after testing, illustrating the lengths of two delaminated portions.

Once the delaminated edge portions 24 have been located, the respective delamination length DL of each can be measured. Those delamination lengths DL, associated with the given coated metal blank 10c, can be added together in order to arrive at a composite delamination length for a given measurement portion of that test part. That composite delamination length can be mathematically compared to a total edge length for the portion of the test piece being measured. When the edge delamination is measured along the length of the elongate strip section 12c, the total edge length of the elongate strip section 12s may be taken as two times the strip length SL, to account for the length of each elongate edge portion. It is to be understood that the total edge length could be based on the initial length of each elongate edge portion (i.e., used here, as it is easiest to measure that length while the elongate strip section 12c is straight and flat), or, alternatively, the final edge length upon twisting could be used. Whichever length is to be used for the mathematical comparison may be noted with the test results so the test basis could be ascertained by the user of the test data. The mathematical comparison of the composite delamination length to the total edge length might, for example, be expressed in the form of a fraction (i.e., composite delamination length/total edge length) or as a percentage of edge delamination. Further, the mathematical comparison could be a comparison of delaminated portions relative to non-delaminated (i.e., coating retained) portions (i.e., (composite delamination length)/(total edge length−composite delamination length)). In an embodiment, that comparative basis is reported with any test results, in order for the user of the data to better understand the data.

In an embodiment, the test results are then compared to a baseline in order to determine whether a given coated test blank 10c passed the twist delamination test as described herein. In one variation, a maximum delamination rating of 30% may be chosen for the baseline for testing parts in this manner. However, it is to be understood that, if more stringent warranty levels are required and/or more difficult use conditions are expected, a company could, for example, choose instead to have a benchmark level of 20%. The point is that the maximum delamination rating, whether expressed as a fraction/decimal or a percentage, may be chosen by a given company/testing facility, based upon such factors as desired lifetime, expected use environment and/or use conditions, etc.

In one embodiment, the test sample of the current invention (e.g. coated test piece 10c) includes a substrate piece or test blank 10 and a coating. The test piece 10 may be laser cut from a metallic sheet (not shown) and surface treated upon cutting, with the substrate piece 10 including an elongate portion 12 with a pair of elongate edges 18. The coating is formed on the substrate piece 10. The parameters used for the laser cutting, surface treatment, and coating steps may be chosen to correspond to parameters used for a production process. The coating, for example, may be a paint composition.

According to one embodiment, a method of testing for edge-based coating delamination includes a series of steps that ultimately facilitate delamination measurement. A coated elongate metal test blank is provided. The coated test blank defines at least two coated edges and a first blank end and a second blank end, with each coated edge having an associated total edge length. The first blank end is mounted in a fixture such that a remainder portion of the coated test blank extends away from the fixture. The second blank end is gripped and, while being gripped, the remainder portion of the coated test blank is twisted a defined rotational amount (e.g. between 1 and 2 full rotations). Each coated edge is then observed for any delaminated edge portions after the twisting step. The length of any delaminated edge portions associated with either coated edge is measured, and the respective lengths of any delaminated edge portions are added to arrive at a composite delaminated edge length for the coated test blank. The composite delaminated edge length is mathematically compared to the combined edge lengths of the coated test blank.

All references cited herein are hereby incorporated by reference to the extent not inconsistent with the disclosure herewith.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art.

Every formulation or combination of components described or exemplified can be used to practice the invention, unless otherwise stated. Specific names of compounds are intended to be exemplary, as it is known that one of ordinary skill in the art can name the same compounds differently. One of ordinary skill in the art will appreciate that methods, device elements, starting materials and synthetic methods other than those specifically exemplified can be employed in the practice of the invention without resort to undue experimentation. All art-known functional equivalents, of any such methods, device elements, starting materials and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The above definitions are provided to clarify their specific use in the context of the invention.

Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

I claim:

1. A method for testing for delamination of a coating from a metallic sheet test piece, the method comprising the steps of:
   a. Providing a test piece comprising a metallic sheet substrate at least partially coated with a coating, the test piece being elongated and characterized by a test piece length, a longitudinal axis, a pair of opposed faces defining the test piece thickness, a pair of opposed longitudinal edges, and a first and a second end;
   b. Establishing a first constrained portion at the first end of the coated test piece by mounting the first end of the test piece in a fixture, the first constrained portion having a first constrained length;
   c. Establishing a second constrained portion at the second end of the coated test piece by gripping the second end of the test piece, the second constrained portion having a second constrained length thereby also establishing a free length of the coated test piece between the first and second constrained lengths;
   d. While maintaining the first and second constrained portions of steps b and c, twisting the second end of the coated test piece by rotating the second end of the coated test piece a predetermined amount about the longitudinal axis at the second end of the coated test piece, thereby also twisting at least a portion of the free length of the coated test piece;
   e. After step d, measuring at least one of:
      the total delamination length on the pair of opposed longitudinal edges over a measurement portion of the free length of the coated test piece; and the total delamination area on the pair of coated opposed faces over a measurement portion of the free length of the coated test piece;
f. Comparing at least one of:
the total delamination length of step e to the total length of the pair of opposed longitudinal edges over the measurement portion of the free length of the test piece; and
the total delamination area of step e to the total area of the coated pair of opposed faces over the measurement portion of the free length of the test piece.

2. The method of claim 1, wherein the test piece comprises a strip portion characterized by a width and a length, the width of the strip portion being at least twice the test piece thickness and the length of the strip portion being at least five times the width of the strip portion.

3. The method of claim 2, wherein the length of the measurement portion is equal to the free length of the test piece.

4. The method of claim 2, wherein the test piece further comprises a plate portion located at the second end of the test piece and connected to the strip portion, the width of the plate portion being at least twice the width of the strip portion.

5. The method of claim 4, wherein the length of the measurement portion is the length between the junction of the plate portion and the strip portion and the first constrained length.

6. The method of claim 1, wherein the thickness of the test piece is from 0.75 mm to 6.5 mm.

7. The method of claim 1, wherein the strip width is from 0.5 to 3 inches.

8. The method of claim 1, wherein the strip length is from 4 to 36 inches.

9. The method of claim 8, wherein the strip length is from 6 to 18 inches.

10. The method of claim 1, wherein the second end of the test piece is rotated from 360 to less than 720 degrees.

11. The method of claim 10, wherein the second end of the test piece is rotated from 540 to less than 720 degrees.

12. The method of claim 1, wherein the total delamination length on the pair of coated opposed longitudinal edges over a measurement portion of the free length of the coated test piece is measured.

13. The method of claim 12, wherein the ratio of the measured total delamination length to the total length of the pair of opposed longitudinal edges over the measurement portion of the coated test piece is compared to an edge delamination baseline value.

14. The method of claim 1, wherein the total delamination area on the pair of coated opposed faces over a measurement portion of the free length of the coated test piece is measured.

15. The method of claim 14, wherein the ratio of the measured total delamination area to the total area of the pair of coated opposed faces over the measurement portion of the test piece is compared to a face delamination baseline value.

16. The method of claim 1, wherein the coating is a paint composition.

17. The method of claim 1, wherein the substrate piece is cut from the sheet metal with a laser.

18. The method of claim 17, wherein the substrate piece is subject to an oxide removal step after cutting and before coating.

19. A test piece,
the test piece being elongated and characterized by a test piece length, a longitudinal axis, a pair of opposed faces defining the test piece thickness, a pair of opposed longitudinal edges, and a first and a second end;
the test piece comprising a metallic sheet substrate piece at least partially coated with a coating and further comprising:
a strip portion characterized by a strip width and a strip length, the width of the strip portion being at least twice the test piece thickness and the length of the strip portion being at five times the width of the strip portion; and
a plate portion located at one of the first and the second end of the test piece and connected to the strip portion, the width of the test piece in the plate portion being at least twice the width of the strip portion;
wherein at least the opposed faces and the opposed longitudinal edges of the strip portion of the test piece are coated with the coating.

20. The test piece of claim 19, wherein the coating is a paint coating.

* * * * *